(12) United States Patent
Kalidindi

(10) Patent No.: US 9,750,778 B2
(45) Date of Patent: Sep. 5, 2017

(54) TERMINALIA CHEBULA AND TERMINALIA BELLIRICA EXTRACTS FOR INHIBITION OF XANTHINE OXIDASE

(71) Applicant: Natreon, Inc., New Brunswick, NJ (US)

(72) Inventor: Sanyasi R. Kalidindi, Monroe, NJ (US)

(73) Assignee: Natreon, Inc., New Brunswick, NJ (US)

( * ) Notice: Subject to any disclaimer, the term of this patent is extended or adjusted under 35 U.S.C. 154(b) by 27 days.

(21) Appl. No.: 14/459,046

(22) Filed: Aug. 13, 2014

(65) Prior Publication Data
US 2015/0050369 A1    Feb. 19, 2015

Related U.S. Application Data

(60) Provisional application No. 61/865,233, filed on Aug. 13, 2013.

(51) Int. Cl.
*A61K 36/61* (2006.01)
*A61K 36/185* (2006.01)

(52) U.S. Cl.
CPC ............ *A61K 36/185* (2013.01); *A61K 36/61* (2013.01)

(58) Field of Classification Search
None
See application file for complete search history.

(56) References Cited

U.S. PATENT DOCUMENTS

| | | | |
|---|---|---|---|
| 6,730,332 B2 | 5/2004 | Agarwal et al. | |
| 7,618,663 B2 | 11/2009 | Palpu et al. | |
| 8,445,033 B2 * | 5/2013 | Vaidya | A61K 36/185 424/725 |
| 9,155,768 B2 * | 10/2015 | Gutmann | A61K 45/06 |
| 2002/0022060 A1 * | 2/2002 | Mathur | A61K 36/185 424/725 |
| 2004/0258775 A1 * | 12/2004 | Patel | A61K 36/185 424/745 |
| 2005/0008710 A1 * | 1/2005 | Subbiah | A61K 36/00 424/725 |
| 2005/0084547 A1 * | 4/2005 | Subbiah | A61K 31/704 424/740 |
| 2005/0227910 A1 * | 10/2005 | Yang | A61K 9/0024 424/422 |
| 2006/0147555 A1 * | 7/2006 | Tripathi | A61K 36/185 424/725 |
| 2006/0280698 A1 * | 12/2006 | Gupta | A61K 8/97 424/50 |
| 2007/0065456 A1 * | 3/2007 | Woods | A61K 31/045 424/195.17 |
| 2010/0202980 A1 * | 8/2010 | Fogel | A61K 36/605 424/48 |
| 2010/0203178 A1 * | 8/2010 | Gupta | A61K 9/08 424/769 |
| 2012/0034325 A1 * | 2/2012 | Vaidya | A61K 36/185 424/734 |

FOREIGN PATENT DOCUMENTS

| | | |
|---|---|---|
| CN | 102309681 A | 1/2012 |
| CN | 102441081 A | 5/2012 |
| JP | H11116497 A | 4/1999 |
| WO | 2007/057924 A1 | 5/2007 |
| WO | 2010/093191 A2 | 8/2010 |
| WO | 2011/119592 A1 | 9/2011 |
| WO | 2013/155175 A1 | 10/2013 |

OTHER PUBLICATIONS

Caraka Sa¼hit¢ —Edited & translated by P.V Sharma,vol. II : Chaukhamba Orientalia, Varanasi, Edn. 5th, 2000. [Time of origin 1000 BC—4th century ] (one page print-out from Traditional Knowledge Digital Library (TKDL).*
Cheng et al. Antioxidant and Free Radical Scavenging Activities of Terminalia Chebula; Biol. Pharm. Bull. 26(9) 1331-1335 (2003).*
Gupta, P.C. Biological and Pharmacological Properties of Terminalia Chebula Retz. (Haritaki)—An Overview; Int. J. of Pharmacy and Pharmaceutical Sciences; vol. 4, Sup. 3, 2012, pp. 62-68.*
Latha et al. Influence of Terminalia bellerica Roxb. Fruit Extracts on Biochemical Paramters in Streptozotocin Diabetic Rats; Int. J. of Pharmacology 6 (2): 89-96 (2010).*
Naik et al. Free Radical Scavenging Reactions and Phytochemcial Analysis of Triphala, an Ayurvedic Formulation; Current Science, vol. 90, No. 8, Apr. 25, 2006.*
Shen et al. Tannins and Related Compounds Isolated From Terminalia Bellerica; Planta Med 2010; 76-P56, 7 pages.*
Wikipedia: Hyperuricemia; Online, URL: <https://web.archive.org/web/20120203161708/http://en.wikipedia.org/wiki/Hyperuricemia> ,Feb. 3, 2012, 3 pages.*
Naik,GH; Priyadarsini, KI; Mohan,H "Free radical scavenging reactions and phytochemical analysis of triphala, an ayurvedic formulation" Current Science, Apr. 25, 2006, 90(8), 1100-1105.*
Gao, et al., "Inhibitory effect on alpha-glucosidase by the fruits of Terminalia chebula Retz.," Food Chem. (2007) 105:628-634.
H-S. Lee, et al., "Antioxidant Effects of Aqueous Extract of Terminalia chebula in Vivo and in Vitro," Biol. Pharm. Bull. (2005) 28(9) :1639-1644.
Mahesh, et al., "Effect of Terminalia chebula aqueous extract on oxidative stress and antioxidant status in the liver and kidney of young and aged rats," Cell Biochem. Funct. (2009) 27:358-363.
Pfundstein, et al., "Polyphenolic compounds in the fruits of Egyptian medicinal plants (*Terminalia bellerica, Terminalia chebula* and *Terminalia horrida*): Characterization, quantitation and determination of antioxidant capacities," Phytochemistry (2010) 71:1132-1148.
Saraswathi Motamarri et al., "Terminalia belerica Roxb-A Phytopharmacological Review," Intl. J. of Research in Pharmaceutical and Biomedical Sciences, vol. 3 (1) Jan.-Mar. 2012 96-99 (2012).
Soni et al., "Febuxostat: The New Generation novel xanthine oxidase Inhibitors," Internationale Pharmaceutica Sciencia, vol. 1, issue 1, Jan.-Mar. 2011 107-115.

(Continued)

*Primary Examiner* — Chris R Tate
*Assistant Examiner* — Aaron J Kosar
(74) *Attorney, Agent, or Firm* — Amin Talati Upadhye LLP; Adam D. Sussman; George M. Carrera, Jr.

(57) ABSTRACT

Compositions containing extracts of *Terminalia chebula* and *Terminalia bellerica*, or combinations thereof and methods for treatment of uricemia, hyperuricemia, and gout in a human subject are provided.

11 Claims, No Drawings

(56) References Cited

OTHER PUBLICATIONS

Hazra et al., "Comparative study of the antioxidant and reactive oxygen species scavenging properties in the extracts of the fruits of Terminalia chebula, Terminalia belerica and Emblica officinalis," BMC Complementary and Alternative Medicine (2010) 10:20.

Khan, "The effect of regular intake of Terminalia chebula on oxidative stress in mice originated from *Salmonella typhmurium*," EurAsia J. BioSci. (2009) 3:113-21.

Ballabh et al., "Traditional medicinal plants of cold desert Ladakh—Used against kidney and urinary disorders," Jul. 23, 2008, vol. 118, issue 2, pp. 331-339 (abstract).

Soni et al., "Febuxostat: The New Generation novel xanthine oxidase Inhibitors," Internationale Pharmaceutica Science, vol. 1, issue 1, Jan.-Mar. 2011 107-115.

Latha, R.C., et al., Therapeutic potential of octyl gallate isolated from fruits of Terminalia bellerica in streptozotocin-induced diabetic rats. Pharm Biol. Jun. 2013;51(6):798-805.

Bag, A., et al., Therapeutic potential of Terminalia chebula Retz. Asian Pac J Trop Biomed. Mar. 2013;3(3):244-52.

Baliga, M. S. et al. Scientific Validation of the Ethnomedicinal Properties of the Ayurvedic Drug Triphala: A Review. Chin J Integr Med. Dec. 18, 2012;(12):946-954.

Chauhan, V., Treatment of Gout Pain With Effective Herbal Medicines. https://web.archive.org/web/20120918011905/http://www.drvikram.com/gout.php. May 28, 2012.

Sarkar, R., et al., Hydroalcoholic extracts of Indian medicinal plants can help in amelioration from oxidative stress through antioxidant properties. J Complement Integr Med. 2012;9:Article 7.

Babita, Y., et al., A Perspective Study of Haritaki. IJRAP. 2011; 2 (5) 1466-1470.

Hazra, B., et al., Comparative study of the antioxidant and reactive oxygen species scavenging properties in the extracts of the fruits of Terminalia chebula, Terminalia belerica and Emblica officinalis. BMC Complement Altern Med. May 13, 2010;10:20.

Latha, R.C., et al., Influence of Terminalia bellerica Roxb. Fruit Extracts on Biochemical Parameters in Streptozotocin Diabetic Rats. International Journal of Pharmacology. 2010;6 (2): 89-96.

Naik, G. H., et al., Studies on the aqueous extract of Terminalia chebula as a potent antioxidant and a probable radioprotector. Phytomedicine II. (2004);530-538.

Juang, L.J., et al., Determination of hydrolyzable tannins in the fruit of Terminalia chebula Retz. by high-performance liquid chromatography and capillary electrophoresis. J. Sep. Sci. 2004; 27, 718-724.

Park, J.O., et al., Effect of Terminalia chebula on Physiological Activity in Mice. Korean Society of Life Science (F) Pusan Life Science Society. Feb. 28, 2004;14(1), 148-153. Abstract Only.

Sodhala; Gadanigrahah ed, Ganga Sahaya Pandeya & Com. Indradeva Tripathi, Part 2 (Kaya cikitsa Khanda) Cahaukhamba Sanskrit Sansthan (Varanasi) Ed. 3rd 1997, p. 527-528.

Mohammad Akbar Arzani; Qaraabaadeen Qaadri (17th century AD), Ahmadi Publication. Delhi, 1968 AD, p. 337.

Ali Ibn e Abbaas Majoosi; Kaamil al Sena'ah, Part II (10th century) AD). Central Council for Research in Unani Medicine, 61 65 Institutional Area, Janak Puri, New Delhi 58, 2005 AD p. 558.

Ayurveda Sarasamgrahah Shri Baidyanath Ayurveda Bhavan Limited, Calcutta. Edn. 2003, p. 523-524.

Susruta; Susruta Samhita Edited & translated by P.V Sharma. vol. II: Chaukhamba Visvabharati, Varanasi. Edn. 1st. 2000. [Time of origin 1000 BC 5th century] p. 318.

Ayurveda Sarasamgrahah Shri Baidyanath Ayurveda Bhavan Limited, Calcutta, Edn. 2003, p. 561.

Bhavamisra; Bhavaprakasa Edited & translated by Brahmasankara Misra, Part II: Chaukhamba Sanskrit Sansthan, Varanasi, Edn. 7th, 2000. [Time of origin 16th century] p. 307.

Bharata Bhaisajya Ratnakara Compiled by Nagmadasa Chaganalala Saha,Translated by Gopinath Gupta vol. IV: B . Jain Publishers. New Delhi, Edn. 2nd. Reprint, Aug. 1999. [This book contains back references from 1000 B.C. to 20th century] p. 19.

\* cited by examiner

TERMINALIA CHEBULA AND TERMINALIA BELLIRICA EXTRACTS FOR INHIBITION OF XANTHINE OXIDASE

This application claims the benefit of earlier filed U.S. Provisional Application No. 61/865,233, filed on Aug. 13, 2013, which is hereby incorporated by reference herein.

FIELD OF THE INVENTION

The present invention relates to extracts of *Terminalia chebula* and *Terminalia bellerica*, or combinations thereof. This invention further relates to use of said extract compositions for treatment of hyperuricemia and gout by inhibition of xanthine oxidase (XO).

BACKGROUND

*Terminalia chebula* Retz. (Combretaceae) ("TC") has been extensively used in Ayurveda, Unani and Homoeopathic systems of medicines for improvement of different health conditions, e.g., constipation, diarrhoea, ulcers, gastroenteritis, asthma, cough, dyspnea, dyspepsia, hemorrhoids, candidiasis, parasites, malabsorption syndrome, hepatomegaly, vesicular and renal calculi, urinary discharges, tumors, skin diseases, leprosy, intermittent fever, rheumatism, arthritis, gout, neuropathy, paralysis, memory loss, epilepsy, depression, leucorrhea, diabetes, cardiovascular diseases, anorexia, and wounds, among others (See, B. Das, *Materia Medica of Ayurveda* (New Delhi: B. Jain Publishers, 1991), p. 8; K. R. Kirtikar and B. D. Basu, "*Terminalia chebula.*" In: *Indian Medicinal Plants*, (2$^{nd}$ Edn., Allahabad, India: Lolit Mohan Basu Publication, 1935), pp. 1020-23; and P. V. Sharma, *Dravya Guna Vigyana* (Vol. 2, Varanasi: Chaukhamba Bharati Academy, 1995), pp. 753-58). *T. chebula* fruit and its different solvent extractives were reported to exhibit hepatoprotective, cardioprotective, antimutagenic/anticarcinogenic, cytoprotective, radioprotective, antioxidant and adaptogenic, antimicrobial, antifungal, antiviral, antiamoebic, immunomodulatory, antidiabetic, wound healing, antispasmodic, and purgative activities in various animal models (S. S. Tasduq, et al., *Human and Exp. Toxicol.* (2006) 25: 11-18; H. Y. Cheng, et al., *Biol. Pharm.Bull.* (2003) 26:1331-5; S. Kaur, et al., *Mutagen Res.* (1998) 419: 169-79; Suthienkul, et al., *South-East Asian Journal Trop. Med., Public Health* (1993) 24: 751-5; Ahmad, et al., *J. Ethnopharmacol.* (1998) 62: 183-93; and N. K. Rao, et al., *BMC Complement Altern. Med.* (2006) 6: 127-32).

*Terminalia chebula* (*T. chebula*) is rich in tannoid principles. The chief constituent tannoids in the fruit are chebulinic acid, chebulagic acid, corilagin and a tannoid metabolite, gallic acid (J. Bruneton. *Pharmacognosy, Phytochemistry, Medicinal Plants.* (Paris, France: Laviosier Publishing, 1995), p. 333). Other minor hydrolyzable tannoids reported in *T. chebula* include punicalagin, chebulanin, neochebulinic acid, 1,2,3,4,6-penta-O-galloyl-β-D-glucose, 1,6,-di-O-galloyl-D-glucose, casuarinin, 3,4,6-tri-O-galloyl-D-glucose, and terchebulin (L. J. Juang, et al., *J. Sep. Sci.* (2004) 27: 718-24). One source lists *T. chebula* as having a tannoids content of about 32% by weight (W. Evans. *Trease and Evan's Pharmacology.* (14th Ed., W. B. Saunders Co. Pvt. Ltd., 1996), p. 493). Other constituents reported in *T. chebula* include fructose, amino acids, succinic acid, beta-sitosterol, resin and purgative principles of anthroquinone, sennoside, flavonol glycosides, triterpenoids and coumarin conjugated with gallic acids (E. Creencia, et al., *KIMIKA* (1996) 12: 1-10).

Chemical constituents isolated from *T. chebula* may vary considerably in type and/or concentration due to a number of factors, e.g., ecological variation, soil variation, and nutrient variation, as well as variations in the process of extraction.

*Terminalia bellirica* (Gaertn.) Roxb. (a.k.a. as *Terminalia bellerica*) ("TB") is grown widely throughout India, Sri Lanka, and South East Asia. *T. bellirica* has been used for centuries in Ayurveda, and contains several constituents in common with *T. chebula* (Saraswathi, et al., *Intl. J. Res. Pharm. Biomed. Sci.* (2012) 3(1):97-99).

Xanthine oxidase ("XO") is an enzyme that catalyzes the oxidation of hypoxanthine to xanthine and can further catalyze the oxidation of xanthine to uric acid. This enzyme plays an important role in the catabolism of purines in some species, including humans. However, sustained elevation of uric acid in blood can cause various diseases, including gout. In patients having gout, excess uric acid result in uric acid crystals which accumulate in cartilage, ligament and surrounding tissues causing severe inflammation and pain.

A xanthine oxidase inhibitor (XO inhibitor) is any substance that inhibits the enzymatic activity of XO, an enzyme involved in purine metabolism. In humans, inhibition of XO reduces the production of uric acid, and several medications that inhibit XO are indicated for treatment of hyperuricemia and related medical conditions including gout. XO inhibitors are also being investigated for management of reperfusion injury. Thus the therapeutic area relevant to XO inhibitors may include stroke, myocardial ischemia, hypertension, diabetes, reperfusion of liver, kidney and lungs, atherosclerosis, hypercholesteremia, inflammatory bowel disease (IBD), among others (Soni, et al., *Intl. Pharm. Scientia* (2011) 1(1):107-114).

The classes of XO inhibitors include purine analogues (such as allopurinol and oxypurinol), inositols (phytic acid and myo-inositol), and febuxostat (a phenylthiazole). WO 1992/009279 describes the inhibitory effect of thiazoles and phenyl derivatives against xanthine oxidase, and WO 2008/126898 reports that indole compounds exhibit an inhibitory effect against xanthine oxidase. Recently, WO 2010/093191 reported a series of indole-thiazole compounds having uric acid lowering properties and having potency similar to febuxostat. These products, however, have side effects, some of them serious, and it would be desirable to have non-toxic plant derived products, substantiated by proof of clinical efficacy, to treat hyperuricemia.

In view of the above, two Ayurvedic products, *Terminalia chebula* and *Terminalia bellerica* were studied in-vitro to determine their xanthine oxidase inhibitory activity and clinically in humans to determine their efficacy to lower Serum Uric acid levels.

SUMMARY

In an embodiment, the present invention relates to extracts of *Terminalia chebula* and *Terminalia bellerica*, or combinations thereof and methods for treatment or prevention of uricemia, hyperuricemia, and gout are provided. In a further embodiment, the invention relates to use of said extract compositions for treatment of hyperuricemia and gout by inhibition of xanthine oxidase (XO).

In one embodiment, a method of treating or preventing uricemia, hyperuricemia, and gout in an individual includes administering to the individual in need of such treatment a therapeutically effective amount of a *T. chebula* extract.

In another embodiment, a method of treating or preventing uricemia, hyperuricemia, and gout in an individual includes administering to the individual in need of such treatment a therapeutically effective amount of a *T. bellerica* extract.

In another embodiment, effective combinations of *T. chebula* extract and *T. bellerica* extract may also be administered.

DETAILED DESCRIPTION

As described above, fruits of *Terminalia chebula* (TC) and *Terminalia bellerica* (TB) have been used in Ayurveda, the traditional Indian system of medicine, for many centuries. The chemical constituents of these fruits are known to be excellent anti-oxidants. Xanthine oxidase (XO) is a key generator of oxygen derived free radicals in the skin and the body through the generation of superoxide anions ($O_2^{\bullet-}$). In one embodiment the activities of TB and TC were tested to determine the effect on the activity of XO, as measured by the quantification of the XO generated reactive oxygen species, in vitro.

As described above, gout is caused by an elevated level of uric acid in the body, indicating the condition in which uric acid crystals accumulate in cartilage, ligament and surrounding tissue inducing severe inflammation and pain. Gout is a kind of inflammatory articular disease, and its incidence rate has steadily increased during past 40 years (N. L. Edwards, *Arthritis & Rheumatism* (2008) 58:2587-2590).

From the 1960's to the mid-1990's, gout patients in the West exhibited an astonishing increase of about 200-300%, mainly in males. The increased rate of gout patients can be traced to obesity, aging, kidney function decline, hypertension, etc. The incidence rate of gout appears to be a level of about 1.4/1,000 persons, but it also depends on the uric acid level. That is, while the incidence rate of gout is 0.5% in a patient group with a blood uric acid level of 7.0 mg/dl or more, the incidence rate of gout is 5.5% in a patient group with a uric acid level of 9.0 mg/dl or more (G. Nuki, *Medicine* (2006) 34:417-423). Considering the incidence rate as described above, blood uric acid level is found to be an important causative factor for gout. In addition, dietary habits, alcohol, lipid and obesity can serve as important inducing factors of gout. Recently, the correlation of uric acid with heart failure, hypertension, diabetes and cardiovascular diseases has been extensively investigated by many researchers, and consequently the importance of uric acid control has been increased (D. I. Feig et al., *New Engl. J. Med.* (2008) 23:1811-1821). In addition, as an inhibitor of xanthine oxidase, allopurinol is known to have an effect on ulcerative colitis (*Aliment. Pharmacol. Ther.* (2000) 14:1159-1162; WO 2007/043457).

Recent increase in the prevalence and incidence of hyperuricemia might be explained by similar increases in adverse lifestyle habits such as purine rich diets and excess alcohol consumption other important factors are obesity, increasing diuretic use, and increasing aging in the population. Asymptomatic hyperuricemia is common and found in about 5 to 8% of adult males. When serum uric acid level is greater than 9.0 mg/dl, the probability of progression to clinical gout is six times higher. Hyperuricemia is not only a risk factor for renal disease progression, but also may affect patient survival by inducing or aggravating cardiovascular disease. Increased uric acid may reflect tissue hypoxia or increased oxygen free radical formation, which is related closely to cardiovascular pathology. Most studies have linked hyperuricemia to poor clinical outcomes due to its marked association with cardiovascular disease (CVD) and renal disease.

*Terminalia bellerica* and *Terminalia chebula* along with other exotic species have reportedly shown effect against problems involving urine discharge, burning sensation and painful urination, inflammation and bleeding in the kidney, and removal of blockage by urine and kidney stones (Basant Ballabh, O. P., et al., *Journal of Ethnopharmacology* Volume 118, Issue 2, 23 Jul. 2008, Pages 331-9).

The anti-oxidant property of *Terminalia bellerica* and *Terminalia chebula* has been demonstrated in several studies (Hazra et al., "Comparative study of the antioxidant and reactive oxygen species scavenging properties in the extracts of the fruits of *Terminalia chebula*, *Terminalia belerica* and *Emblica officinalis*," *BMC Complementary and Alternative Medicine* (2010) 10:20; and Kishwar Hayat Khan, "The effect of regular intake of *Terminalia chebula* on oxidative stress in mice originated from *Salmonella typhimurium*," *EurAsia J. BioSci.* (2009) 3:113-21). However, in-vitro studies are not always predictive of a product's clinical efficacy. Thus, in-vitro xanthine oxidase inhibitory activity as well as clinical efficacy of the extracts of *Terminalia chebula* and *Terminalia bellerica* have been conducted.

In an embodiment, a *Terminalia chebula* extract containing a hydrolyzable tannoid blend is provided. A general method for extracting *Terminalia chebula* to obtain an enriched hydrolyzable tannoid powder is provided.

Studies cited above used extracts of *T. chebula* fruit pericarp. However, *T. chebula* contains several bioactive components, including chebulagic acid, chebulinic acid, chebulic acid and other low molecular weight hydrolyzable tannoids (LMwHTs). Many studies, some of which are described below, have also been done on the individual bioactives of *T. chebula*.

Tannins may be divided into two groups: (a) hydrolyzable tannoids (HTs), which are esters of a polyol or sugar, usually glucose, with one or more trihydroxybenzenecarboxylic acids (i.e., gallates), and (b) derivatives of procyanidins, flavanols or flavanones, so-called condensed tannins HTs are molecules with a polyol (polyfunctional alcohols, generally D-glucose or its derivatives and phenols, namely galloyl and ellagoyl moieties) as a central core. The hydroxyl groups of these carbohydrates are partially or totally esterified with phenolic carboxylic acids like gallic acid (gallotannins), ellagic acid (ellagitannins) or both (gallo-ellagitannins).

Chebulagic acid, depicted in the compound of formula (1), is a tannoid (low Mw polyphenolic) member of the tannin family and has been found as a constituent in many medicinal plants. Chebulagic acid is chemically named as beta-1-O-galloyl-2,4-chebuloyl-3,6-(R)-hexahydroxydiphenoyl-D-glucose.

(1)

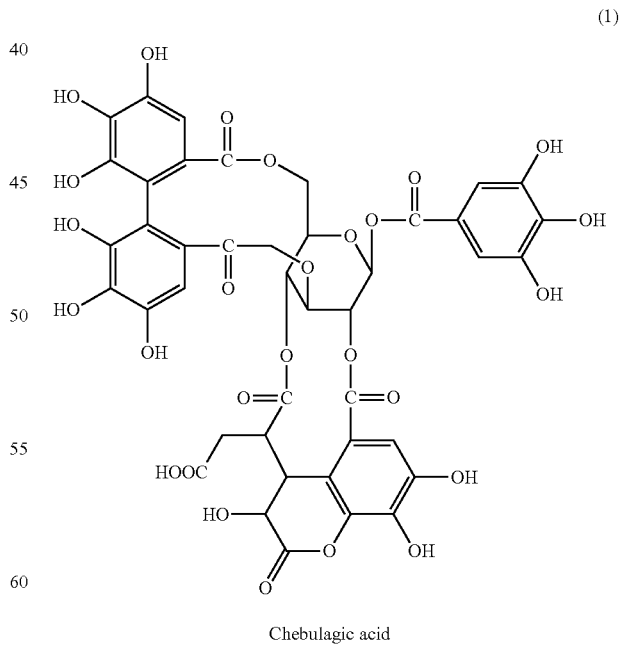

Chebulagic acid

Hydrolyzable tannoids have been reported as key bioactive components of *T. chebula*. Chebulagic acid and chebulinic acid are the two major bioactive hydrolyzable tannoids of *T. chebula*. Chebulagic acid ("CA"), a natural antioxidant, has shown potent anti-inflammatory effects in LPS-stimulated RAW 264.7, a mouse macrophage cell line. These effects were exerted via inhibition of NO and PGE$_2$ production and down-regulation of iNOS, COX-2, 5-LOX, TNF-α and IL-6. CA inhibited NF-κB activation by LPS, and this was associated with the abrogation of IκB-α phosphorylation and subsequent decreases in nuclear p50 and p65 protein levels (D. B. Reddy, et al., Biochemical *and Biophysical Research Communications*. (2009) 381: 112-117).

Chebulagic acid has shown potent COX-LOX dual inhibition activity with IC$_{50}$ values of 15±0.288, 0.92±0.011 and 2.1±0.057 μM for COX-1, COX-2 and 5-LOX, respectively. CA also exhibited anti-proliferative activity against HCT-15, COLO-205, MDA-MB-231, DU-145 and K562 cell lines. Further mechanistic studies on COLO-205 cells revealed induction of apoptosis by chebulagic acid (D. B. Reddy, et al., *J Ethnopharmacol*. (2009) 124: 506-12).

Chebulagic acid, isolated from *Terminalia chebula* Retz, proved to be a reversible and non-competitive inhibitor of maltase with a K(i) value of 6.6 μM. The inhibitory influence of chebulagic acid on the maltase-glucoamylase complex was more potent than on the sucrase-isomaltase complex. The magnitude of alpha-glucosidase inhibition by chebulagic acid was greatly affected by its origin. These results show a use for chebulagic acid in managing type-2 diabetes (Y. N. Huang et al., *Biosci. Biotechnol. Biochem*. (2008) 72: 601-3).

Chebulagic acid has also been shown to synergize the cytotoxicity of doxorubicin in human hepatocellular carcinoma through COX-2 dependent modulation of MDR-1. Chebulagic acid increased the accumulation of doxorubicin in a concentration dependant manner and also enhanced the cytotoxicity of doxorubicin in HepG2 cells by 20 fold. Quantitation of interaction by calculating Combination Index (CI) showed a strong synergistic interaction between chebulagic acid and doxorubicin in terms of cell growth inhibition (C. Achari, et al., *Med Chem*. (2011) 7: 432-42).

Herpes simplex virus 1 (HSV-1) is a common human pathogen that causes lifelong latent infection of sensory neurons. Non-nucleoside inhibitors that can limit HSV-1 recurrence are particularly useful in treating immunocompromised individuals or cases of emerging acyclovir-resistant strains of herpes virus. Chebulagic acid and punicalagin, two hydrolyzable tannoids isolated from the dried fruits of *Terminalia chebula* Retz. (Combretaceae), have been found to inhibit HSV-1 entry at noncytotoxic doses in A549 human lung cells by blocking the interactions between cell surface glycosaminoglycans and HSV-1 glycoproteins (L. T. Lin, et al., *J. Virol*. (2011) 85: 4386-98).

Chebulagic acid has been reported to suppress the onset and progression of collagen-induced arthritis in mice through immune suppression (anticollagen IgG, IL-10, IL-6) via the of TGFbeta and CD4+, CD25+ T cells (P. M. Lee, S. I. Hyun, et al., *Arthritis Rheum*. (2005) 52: 345-53).

Chebulagic acid has been reported to possess cytotoxic properties against PRMI-7951 melanoma cells (Y. Kashiwada, et al., *J. Nat. Prod*. (1992) 55: 1033-43).

Chebulinic acid, depicted in the compound of formula (2), is another tannoid member of the tannin family derived from galloyl glucose. Chebulinic acid is chemically named as 1,3,6-tri-O-galloyl-2,4-chebuloyl-beta-D-glucose.

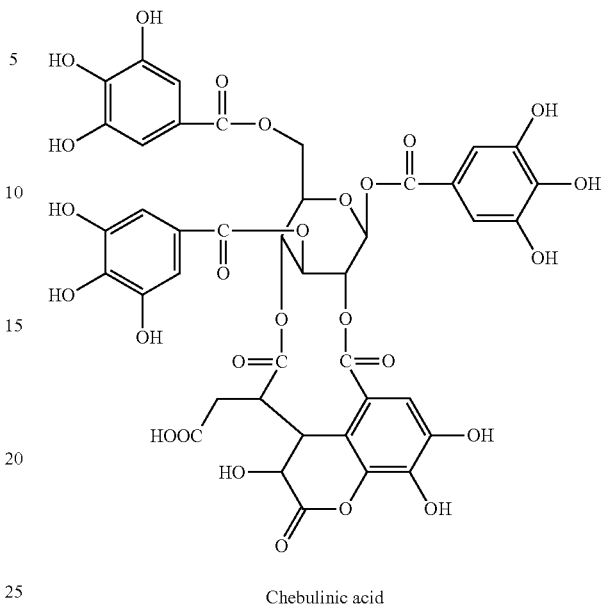

(2)

Chebulinic acid

Chebulinic acid and Tellimagrandin I have been shown to exert anti-tumor properties in human cervical carcinoma HeLa cells (Z. C. Yi, et al., *Cancer Lett*. (2006) 242: 77-87).

Chebulinic acid inhibited the hemoglobin synthesis of butyric acid and hemin-treated K562 cells in a concentration-dependent manner. Chebulinic acid has also been reported to inhibit the erythroid differentiation likely through changing transcriptional activation of differentiation relative genes (Z. C. Yi, et al., *Acta Pharmacol Sin*. (2004) 25: 231-8).

Chebulinic acid, tannic acid and ellagic acid were reported to be the growth inhibitory phenolics of *T. chebula* fruits against malignant cell lines including a human (MCF-7) and mouse (S115) breast cancer cell line, a human osteosarcoma cell line (HOS-1), a human prostate cancer cell line (PC-3) and a non-tumorigenic, immortalized human prostate cell line (PNT1A) (A. Saleem, et al., *J Ethnopharmacol*. (2002) 81: 327-36).

Chebulinic acid has been shown to elicit blood pressure lowering effect in rats, likely mediated via the decrease in cardiac output resulting from reduced left ventricular contraction (Y. Y. Guan, et al., *Clin Exp Pharmacol Physiol*. (1996) 23: 747-50).

Chebulinic acid and punicalin were able to block the binding of HIV rgp120 to CD4. These compounds were not toxic to stimulated human peripheral blood lymphocytes at concentrations ten times above their maximal effective concentration (J. L. Weaver, et al., *Biochem. Pharmacol*. (1992) 43: 2479-80).

Gallic acid (GA) and chebulic acid (CA) were isolated from the extract of the herbal medicine Kashi (myrobalan, the fruit of *T. chebula*) as active principle that blocked the cytotoxic T-lymphocyte (CTL)-mediated cytotoxicity. Granule exocytosis in response to anti-CD3 stimulation was also blocked by GA and CA at the equivalent concentrations (S-I. Hamada, et al., *Biological & Pharmaceutical Bulletin*. (1997) 20: 1017-1019).

Chebulagic acid and chebulinic acid have been shown to possess antifibrotic activity through the inhibition of the Smad pathway (H. Y. Chuang, et al., *J. Sci. Food Agric*.

(2011) 91:2777-84). Chebulagic acid, chebulinic acid, and other phenolics isolated from *T. chebula*, showed stronger DPPH radical scavenging and melanin inhibitory activities than ascorbic acid, butylated hydroxyl toluene, alpha-tocopherol, arbutin and kojic acid (A. Manosroi, et al., *Nat. Prod. Res.* (2010) 24: 1915-26).

The findings for the herb *T. bellerica* are similar, and the phytochemical profiles include common components.

As evidenced by the extensive and significant pharmacological activity of the bioactive constituents and/or components of *T. chebula* and/or *T. bellerica*, there is a need for the extraction process to be optimized to get the highest possible levels of these bioactives.

In an embodiment, the extraction process of the current invention includes the steps of: providing the pericarp of the fruits of *T. chebula* or *T. bellerica*; pulverizing or grinding the the pericarp to a powder; extracting the powder with an extraction solvent or solvent mixture, optionally, with heating, to provide an enriched extract; and concentrating or drying the enriched extract to provide a hydrolyzable tannoid enriched powder. Aqueous solvent is preferred. A particularly preferred solvent is water. Useful extraction temperatures can range from about 25° C. (ambient) to about 90° C. Particularly useful extraction temperatures can range from about 25° C. to about 80° C.

Useful extraction times in conjunction with maintaining the useful temperatures can range from about 2 hours to about 16 hours. A particularly useful extraction time range at about 25° C. is from about 12 hours to about 16 hours. Length and temperature of extraction may be varied at atmospheric pressure (i.e., approx. 1 atm). It is contemplated that pressure can be varied in the extraction process, for example, by use of a commercial pressure reactor apparatus.

The extraction process can also include drying the extracted sample. Suitable drying methods include spray drying, lyophilization, freeze drying, vacuum drying (with or without heating), evaporation (with or without heating), and concentration under vacuum. Once isolated or obtained the hydrolyzable tannoid enriched *T. chebula* extract powder may be processed by any suitable means, including grinding, milling, sieving, sizing, and the like. The obtained hydrolyzable tannoid enriched *T. chebula* extract powder may be prepared in any suitable particle size or particle size range.

In one embodiment, the present invention contemplates a *T. chebula* extract including an optimized hydrolyzable tannoid blend containing not less than about 10-15% of chebulinic acid, not less than about 10-12% of chebulagic acid, and not less than about 10-12% of other low molecular weight hydrolysable tannoids, and/or a *T. bellerica* extract including an optimized hydrolysable tannoid blend containing not less than about 2-3% of chebulinic acid, not less than about 2-3% of chebulagic acid, and not less than about 10% of other low molecular weight hydrolysable tannoids.

In-vitro xanthine oxidase inhibitory activity and clinical efficacy of both *T. chebula* and *T. bellerica* extracts were evaluated as exemplified below:

Example 1

Comparative Antioxidant Activity of *T. chebula* and *T. bellerica* Extracts in In Vitro models of XO Inhibition.

One *T. chebula* (TC) based extract was tested at three different dilutions of 5, 25 and 50 µg/mL, and one *T. bellerica* (TB) based extract was tested at the same three dilutions. Standard positive control was allopurinol (AP) tested at 1, 5 and 10 µg/mL.

Source of tested materials. *T. chebula* and *T. bellerica* extracts were provided by Natreon, Inc., New Brunswick, N.J., USA, and Allopurinol was purchased from Sigma Chemicals, Australia.

Background Regarding Free Radicals and Antioxidants.

Free radicals are atoms or groups of atoms containing at least one unpaired electron in their orbitals, and, in one exemplary route, can be formed when oxygen interacts with certain molecules. Once formed in abundance (or when having a high localized concentration), these highly reactive species can start a chain reaction, causing damage to many biomolecules. Their main danger comes from the damage they can do when they react with important cellular components such as DNA, mitochondria, cellular proteins or the lipids present in the cell membrane (S. F. Pala, et al., *Adv. Mol. Biol.* (2007) 1: 63-69). On the other hand, they play important role in different cellular processes, are involved in cytotoxicity, and as a defense against microorganisms and in neurotransmission, when present in low/moderate amounts (M. Valko, et al., *Int. J. Biochem. Cell Biol.* (2007) 39: 44-84). There are various types of free radicals that can be formed within the body. Reactive oxygen species (ROS) and reactive nitrogen species (RNS) are major components of this "free radical" system. The most deleterious ROS include hydroxyl radical, superoxide radical, singlet oxygen, and the like. The most deleterious RNS include nitric oxide and peroxynitrite anion. In addition to these two types of free radicals, atomic hydrogen, many heavy transition metals (e.g. iron, copper, zinc and manganese), halogenated compounds, many drugs, ionizing radiation, and environmental wastes (e.g. CO, asbestos, ozone, solvents etc.) also behave like sources of free radicals (G. S. Timmins and M. J. Davies, In: Electron Paramagnetic Resonance, The Royal Society of Chemistry, (Cambridge, UK), (1998) 1-49). The most common free radicals and/or oxidants present in the biological systems are described in Table 1 below.

For the purposes of the present disclosure, XO may generate superoxide $O_2^{\bullet-}$ radical.

General Information about the Most Common ROS and RNS Present in Biological Systems.

TABLE 1

| Free radical/Oxidants | Chemical formula | Generating reaction | Damage caused |
|---|---|---|---|
| Hydroxyl | OH$^{\bullet}$ | $Fe^{2+} + H_2O_2 \rightarrow Fe^{3+} + OH^{\bullet} + OH^-$ (Fenton reaction) | Oxidation of almost all types of biomolecules, especially DNA |
| Superoxide | $O_2^{\bullet-}$ | $O_2 + e^- \rightarrow O_2^{\bullet-}$ | Oxidation of Fe—S cluster proteins to release $Fe^{2+}$, responsible for generation of OH$^{\bullet}$ |

TABLE 1-continued

| Free radical/Oxidants | Chemical formula | Generating reaction | Damage caused |
|---|---|---|---|
| Nitric oxide | $NO^{\bullet}$ | Arginine → Citrulline + $NO^{\bullet}$ | Implicated in Juvenile diabetes, multiple sclerosis, arthritis, and ulcerative colitis, when in excess |
| Peroxynitrite anion | $ONOO^-$ | $NO^{\bullet} + O_2^{\bullet-} \rightarrow ONOO^-$ | Implicated in Heart disease, Alzheimer's disease, and atherosclerosis |
| Hydrogen peroxide | $H_2O_2$ | $2O_2^{\bullet-} + 2H^+ + 2e^- \rightarrow H_2O_2 + O_2$ (Dismutation of superoxide radical) | Acts as the source of $OH^{\bullet}$ |

Several enzyme systems within the body neutralize excess free radicals. One important component of the defense system that prevents the body from free radical damage includes antioxidants that can serve as chemical scavengers or quenchers of free radicals. Antioxidants are molecules which can safely interact with free radicals and terminate the chain reaction before vital molecules, or reactive sites, are damaged or chemically modified. Antioxidants are of two types: enzymatic antioxidants and non-enzymatic antioxidants. Enzymatic antioxidants include superoxide dismutase (SOD), glutathione peroxidase (GPx) and catalase (CAT). Non-enzymatic antioxidants include specific bioactive metabolites and several broad classes of agents, such as: ascorbic acid (Vitamin C), α-tocopherol (Vitamin E), glutathione (GSH), carotenoids, flavonoids, polyphenols, and molecules from other natural sources. Under normal physiological conditions, there is a balance between both the activities and the intracellular levels of these antioxidants within a living subject or organism. However, during stress, there may be an imbalance between the required beneficial, protective levels versus the actual physiological levels of these antioxidants in the subject. In these situations, antioxidants from one or more exogenous sources may be needed to overcome the effects of an assault by one or more types of free radicals. An ideal antioxidant should scavenge/neutralize different types of free radicals, e.g. $OH^{\bullet}$, $O_2^{\bullet-}$, $OOH^{\bullet}$, $NO^{\bullet}$ and $ONOO^-$ (or mixtures thereof), present in the biological systems.

Therefore, in embodiments of the present invention, a battery of in vitro antioxidant screens may be used to assess the comparative antioxidant activities of T. chebula and T. bellerica samples prepared according to the principles of the present invention. Useful assays may include: ABTS radical cation decolorisation assay (N. Pellegrini, et al., J. Nutr. (2003) 133: 2812-2819); DPPH radical decolorisation assay (I. Gulcin, et al., J. Ethnopharmacol. (2004) 90: 205-215); FRAP—Ferric reducing assay for plasma: Assay for reduction power (N. Pellegrini, et al.); Hydroxyl radical scavenging assay by 2-deoxyribose degradation method (S. K. Chung, et al., Biosci. Biotech. Biochem. (1997) 61: 118-123); Hydrogen peroxide scavenging assay (I. Gulcin, et al.); Estimation of total phenolic content by Folin-Ciocalteu method (S. A. L. Morais, et al., J. Braz. Chem. Soc. (1999) 10:447-452); Nitric oxide radical scavenging assay (R. Sundararajan, et al., Complementary & Alternative Medicine (2006) 6: 8-14); Peroxynitrite scavenging assay (L. B. Valdez, et al., Medicina (Lithuania), (2007) 43: 306-309); Inhibition of rat erythrocyte membrane lipid peroxidation (T. Moriguchi, et al., J. Nutr. (2001) 131: 1016S-1019S); and, Inhibition of lipid peroxidation of goat brain homogenate (S. K. Mondal, et al., Ind. J. Exp. Biol. (2006) 44: 39-44).

Example 1A

Superoxide radical scavenging assay by NBT (Nitro Blue TetraZolium)—hypoxanthine/XO method (Palanisamy, et al., "Rind of the rambutan, Nephelium lappaceum, a potential source of natural antioxidants." Food Chemistry (2008) 109:54-63).

Stock solutions of test materials were prepared at 20 mg/ml in water (TB and TC) or immediately prior to the experiment. Further dilutions were made in type I sterile water and the effect of test materials on XO-mediated free radical (superoxide) generation was assessed as previously described (Palanisamy et al., 2008), using hypoxanthine/XO/NBT (tetrazolium salt) system with the reaction product (formazan) followed at 570 nm with the BioRad microplate spectrophotometer 3550-UV. Allopurinol (AP) was the positive control, double-distilled water was the negative control (blank). P values representing statistical significance were calculated using paired t-test and threshold of statistical significance was fixed at p=0.05 and at least 15% difference as compared to the water control.

Effect of different products on superoxide generation by XO was determined.

TABLE 2

| Test Material | % Control | P Value |
|---|---|---|
| Water (blank) | 100 | 1.000 |
| TB 5 μg/ml | 46 | 0.000 |
| TB 50 μg/ml | 12 | 0.000 |
| TB 25 μg/ml | 7 | 0.000 |
| TC 5 μg/ml | 53 | 0.000 |
| TC 25 μg/ml | 12 | 0.000 |
| TC 50 μg/ml | 8 | 0.000 |
| AP 1 μg/ml | 89 | 0.008 |
| AP 5 μg/ml | 54 | 0.000 |
| AP 10 μg/ml | 43 | — |

As illustrated in Table 2, TB and TC exhibited a strong, dose-dependent inhibitory activity towards superoxide generating activity of XO.

Effective-Dose 50% (ED50=dose required for 50% inhibition of XO) of tested materials.

TABLE 3

| Test Material | ED50 (μg/ml) |
| --- | --- |
| TB | 5 |
| TC | 6 |
| AP | 6 |

Table 3 shows that the ED50 (dose required for 50% inhibition) was on par with the synthetic gout medicine allopurinol. These experiments demonstrated that both *T. chebula* and *T. bellerica* extracts were effective and potent materials for the inhibition of XO. It is expected that *T. chebula* and *T. bellerica* extracts, or mixtures thereof, will be useful as natural medicines for the treatment of hyperuricemia and gout, among other disease conditions.

Example 1B

Superoxide radical scavenging assay by NBT (Nitro Blue TetraZolium)-NADH (Nicotinamide Adenine Dinucleotide-Reduced)-PMS (Phenazonium Methosulphate) method (I. Gulcin, et al., *J. Ethnopharmacol.* (2004) 90: 205-215, as above).

Superoxide radicals are generated in the mitochondria as useful molecules, but at very low concentrations. At high concentrations, they are potentially as deleterious as hydroxyl radicals. The generated radicals may be tested along with certain antioxidants that may be present in the *T. chebula* and/or *T. bellerica* extracts prepared according to the principles of the present invention, in order to assess antioxidant capacities.

Analytical Method. Test sample solution is prepared by dissolving sample in distilled water at a concentration 1 mg/ml. 20, 40, 60 or 80 μl of sample solution is mixed with 500 μl of each of NADH solution (300 μM in TRIS-HCl), NBT solution (100 μM in TRIS-HCl) and PMS solution (20 μM in TRIS-HCl) to provide a final volume of 2000 μl. Remaining volume is made up with TRIS-HCl. The mixture is incubated for 30 minutes at room temperature for reaction to take place. Then the absorbance of the blue formazan, developed during reaction, is measured at 560 nm against reagent blank. A control sample is prepared with water and without TC (or TB) material. The experiment is conducted in duplicate.

Percent scavenging, as used herein, of the radical is calculated from the following formula, where OD=optical density.

$$\text{Percent scavenging} = \frac{OD_{control} - OD_{sample}}{OD_{control}} \times 100 \quad \text{Equation (1)}$$

Percent scavenging of the radical is calculated as in Equation 1 above. $IC_{50}$ values (concentration which scavenges 50% of the radical) is calculated by plotting percent scavenging on Y-axis and sample concentration on X-axis. Results are then expressed in $IC_{50}$ values. Since trolox commonly does not show sensitivity in this experimental model, it was not used as standard for calculation of trolox equivalents.

It would be expected that the *Terminalia chebula* and/or *T. bellerica* extracts will quench superoxide ($O_2^{\bullet-}$) radicals generated from PMS-NADH reaction mixture. The results are expected to indicate that the extracts are good quenchers of $O_2^{\bullet-}$ radicals. The result thus is expected to indicate that the TC and/or TB extracts are effective and potent materials for radical scavenging, and also the inhibition of XO.

In conclusion, the results of the study demonstrated that both the *Terminalia chebula* extract and the *Terminalia bellerica* extract showed significant antioxidant activity against superoxide radicals generated by XO.

It is further expected that a *Terminalia chebula* extract, or a *Terminalia bellerica* extract, or combinations thereof, made in accordance with the principles of the invention would be effective in treating uricemia, hyepruricemia and gout.

Example 2

Clinical Study

A randomized, double blind, placebo controlled, parallel-group study was performed to evaluate the effect of *Terminalia chebula* and *Terminalia bellerica* in comparison to Febuxostat and a placebo on serum uric acid levels in patients with hyperuricemia.

Clinical trial site: Department of Clinical Pharmacology and Therapeutics; Nizam's Institute of Medical Sciences; Punjagutta, Hyderabad, India. Sponsor: Natreon Inc., New Brunswick, N.J., USA.

Primary objective: To compare the efficacy of *Terminalia chebula*, *Terminalia bellerica* in comparison to Febuxostat and placebo in terms of reduction in serum uric acid levels in hyperuricemic patients.

Secondary objective: To evaluate the safety and tolerability of *Terminalia chebula* and *Terminalia bellerica* in hyperuricemic patients.

Study Design

The present study was a prospective, randomized, double blinded, placebo controlled trial. A total of 52 patients were enrolled to receive the study treatment in a randomized manner. The study was approved by the Institutional Ethics Committee and all the subjects gave written informed consent prior to their participation in the study.

Hyperuricemia patients of either gender aged between 18 and 70 years were selected, with serum uric acid level ≥6.0 mg/dL and ≤12.0 mg/dL after having stopped all uric acid-lowering therapy for at least 10 days. Patients who were willing to comply with the requirements of the study and to give voluntary, written informed consent were enrolled into the study. Patients with a gout flare during screening or baseline visit were excluded. Patients currently using aspirin or other NSAIDS, diuretics, other medications with known urate-lowering effects were also excluded from the study. Patients with history or presence of nephrolithiasis or uncontrolled hypertension or diabetes, hepatic and renal impairment, pregnant or lactating females or secondary hyperuricemia (e.g. due to myeloproliferative disorder, or organ transplant) were excluded.

After screening, all the eligible patients were randomized to either of the four treatment groups in a double blinded fashion for duration of 8 weeks, prospectively 12 weeks.

Group 1—*Terminalia chebula* 500 mg—1 capsule of 500 mg orally twice a day (BID) after food.

Group 2—*Terminalia bellerica* 500 mg—1 capsule of 500 mg orally twice a day (BID) after food.

Group 3—Febuxostat—1 tablet of 40 mg (encapsulated in a similar capsule to that of *Terminalia chebula/Terminalia* bellerica/placebo capsules) once daily (OD) orally in the morning after food and an identical placebo capsule in the evening after food.

Group 4—Placebo capsules (identical to *Terminalia chebula* and *Terminalia bellerica*)—1 capsule orally twice a day (BID) after food.

Subjects were asked to attend follow-up visits at 4 weeks, 8 weeks, and (prospectively) 12 weeks of therapy. At each visit they were evaluated for efficacy measurements and safety assessments. Serum uric acid levels were measured at baseline, end of 4 weeks, and end of 8 weeks.

Safety lab investigations for hematological, hepatic and renal biochemical parameters were done at baseline and at the end of the study (8 weeks) and also as and when required (in case of any adverse drug reaction (ADR)). Subjects were interviewed for the presence of ADR and the same was recorded in the case report form (CRF). Compliance to therapy was assessed by pill count method.

For the purposes of the present study, *Terminalia chebula* is an aqueous extract of the edible fruits of *Terminalia chebula* containing: not less than 15% of Chebulinic acid, not less than 10% of Chebulagic acid, and not less than 15% of other low molecular weight hydrolysable tannins, as standardized by HPLC.

For the present study, *Terminalia bellerica* is an aqueous extract of the edible fruits of *Terminalia bellerica* containing low molecular weight hydrolyzable tannins including chebulinic acid and chebulagic acid as bioactives, and gallic acid and ellagic acid.

Study Procedure

Patients were enrolled into the study after they read, understood and signed the informed consent form. Next they were screened and assessed for the inclusion/exclusion criteria (visit 1). At the baseline/randomization visit (visit 2, day 1), vital signs, general examination, routine lab investigations, serum uric acid levels were performed and all eligible subjects were randomized into the study medication to receive either one of the four treatments as per prior randomization schedule. The study medications were dispensed at randomization visit and compliance checked by pill count method at the next visit, i.e., at the end of 4 weeks.

The subsequent 2 visits were scheduled at 4 weeks interval (visit 3—after 4 weeks of treatment, visit 4—after 8 weeks of treatment), vital signs, general examination; serum uric acid levels were measured. Pill count for study medication was evaluated. At the (prospective) conclusion of the study, Visit 5 (after 12 weeks post treatment), vital signs, general examination, serum uric acid, routine safety lab investigations will be performed. At every visit patient was interviewed regarding any incidence of adverse effect, especially GI intolerance and the same was noted in a case record form. Adverse Effects/SAE monitoring would be done throughout the course of study. Safety lab parameters will be done before and after treatment and as and when required. Participant is given a contact number for reporting and accessing medical help with regard to any adverse event.

Primary Outcome Measures (as Determined Herein):

1. Absolute change in serum uric acid levels from baseline to 4 weeks, 8 weeks, and (prospectively) 12 weeks of treatment.

2. Mean percentage reduction in serum uric acid levels from baseline to 4 weeks, 8 weeks, and (prospectively) 12 weeks of treatment.

Secondary Outcome Measures (as determined herein):

1. Proportion of patients whose serum uric acid levels have decreased to ≤6.0 mg/dl following treatment at the end of 8 weeks/12 weeks.

2. Measurements of Tolerability will be assessed at the end of 8 weeks/12 weeks as: Good—no side effects; Fair—mild to moderate side effects; and/or Poor—severe side effects and withdrawal of therapy.

Statistical Analysis

Study data is expressed as Mean±SD. Primary and secondary outcome measures were analyzed as the mean percentage reduction and absolute change in serum uric acid levels from baseline to 4 weeks, 8 weeks, and (prospectively) 12 weeks of treatment. ANOVA, Paired t test were used to compare the mean change from baseline to post treatment (4, 8 weeks) within group and unpaired t test for between group comparisons. All statistical analysis was performed using the Graph pad PRISM software 4 (Graph pad software Inc. San Diego, Calif., USA).

Results of the Clinical Study

A total of 52 eligible patients were enrolled into the study and completed 8 weeks of treatment so far. Thirteen patients in *Terminalia chebula* 500 mg group, 13 patients in *Terminalia bellerica* 500 mg group, 13 patients in Febuxostat 40 mg group, and 13 patients in placebo group have completed 8 weeks of study treatment.

TABLE 4

(Demographic Data)

| | *Terminalia chebula* 500 mg (A) | *Terminalia bellerica* 500 mg (B) | Febuxostat 40 mg (C) | Placebo (D) |
| --- | --- | --- | --- | --- |
| Total No. | 13 | 13 | 13 | 13 |
| Gender (M/F) | 10/3 | 11/2 | 9/4 | 10/3 |
| Age (yrs) | 56.85 ± 9.48 | 53.07 ± 14.23 | 53.46 ± 9.87 | 53.15 ± 8.15 |
| Weight (Kg) | 66.44 ± 9.34 | 64.80 ± 16.63 | 66.92 ± 10.26 | 66.76 ± 9.80 |
| BMI (Kg/m$^2$) | 24.61 ± 3.63 | 23.79 ± 5.64 | 25.03 ± 2.33 | 23.70 ± 2.11 |

The detailed demographic characteristics of all the four study groups are shown in Table 4. There were no significant differences between treatment groups in baseline characteristics including age, weight & body mass index.

Serum Uric acid levels from baseline to the end of 4 weeks treatment

TABLE 5

|  | Terminalia chebula 500 mg (A) | Terminalia bellerica 500 mg (B) | Febuxostat 40 mg (C) | Placebo (D) |
|---|---|---|---|---|
| Baseline (mg/dl) | 7.47 ± 1.05 | 8.04 ± 0.93 | 8.68 ± 1.05 | 7.45 ± 0.7 |
| Serum Uric Acid level at the end of 4 weeks (mg/dl) | 7.07 ± 0.52 | 7.05 ± 0.71 | 7.23 ± 0.72 | 7.6 ± 0.71 |
| Mean Percentage Reduction in Serum Uric Acid at the end of 4 weeks (%) | −4.5 ± 7.21@*# | −11.75 ± 8.08@*NS | −16.31 ± 5.32*NS | +2.39 ± 4.74#* |

Mean % Reduction of Serum Uric acid levels at the end of 4 weeks treatment:
NS B Vs C (p = ns),
*B vs D (p < 0.001),
*A Vs C, (p < 0.001),
A vs D (p < 0.01)

As shown in Table 5, there was no statistical difference between the baseline Serum uric acid levels of the four groups of treatment.

However, when the mean percentage reduction of Serum Uric acid levels at the end of 4 weeks treatment were compared among the 4 treatment groups, *T. bellerica* at 500 mg BID dosing showed highly significant difference (p<0.001) when compared to placebo, but not with febuxostat, which means that *T. bellerica* is working as well as febuxostat and much better than placebo, statistically speaking. On the other hand, *T. chebula* at 500 mg BID dosing showed significant difference only at p<0.01 level compared to placebo and at p<0.001 level compared to febuxostat. This means that *T. chebula*, though effective, is not as effective as *T. bellerica* in reducing Serum Uric acid levels.

Serum Uric acid levels from baseline to the end of 8 weeks treatment was found that the lowering of Serum Uric acid levels was highly significant for both *T. chebula* 500 mg BID and *T. bellerica* 500 mg BID versus placebo as well as febuxostat (p<0.001). It is interesting to note that the difference between *T. chebula* 500 mg BID and *T. bellerica* 500 mg BID is also statistically highly significant (p<0.001), although the xanthine oxidase inhibitory activity of both of these extracts is similar (Tables 2 and 3). This means that the clinical efficacy of these two extracts in reducing Serum Uric acid levels is not the same despite their similar in-vitro antioxidant activity. Thus, in-vitro studies may not always be predictable of a product's clinical efficacy.

Safety Assessments

All safety haematological and biochemical parameters were within normal limits in all the four treatment groups at the baseline recording. Two patients in the Febuxostat group had elevated mildly elevated total bilirubin, and 1 patient had complained of nausea and vomiting. One patient in the *Terminalia chebula* group had mild GI intolerance. None of

TABLE 6

|  | Terminalia chebula 500 mg (A) | Terminalia bellerica 500 mg (B) | Febuxostat 40 mg (C) | Placebo (D) |
|---|---|---|---|---|
| Baseline (mg/dl) | 7.47 ± 1.05 | 8.04 ± 0.93 | 8.68 ± 1.05 | 7.45 ± 0.7 |
| Serum Uric Acid level at the end of 8 weeks (mg/dl) | 6.82 ± 0.42 | 6.40 ± 0.6 | 6.08 ± 0.6 | 7.9 ± 0.71 |
| Mean Percentage Reduction in Serum Uric Acid Level after 8 weeks (%) | −7.84 ± 7.38* | −19.93 ± 6.74* | −29.58 ± 5.74* | +6.43 ± 9.0* |

Mean % Reduction of Serum Uric acid levels at the end of 8 weeks treatment:
*A Vs D, A Vs C, B Vs D, B Vs C (p < 0.001)

As seen from Table 6, when the mean percentage reduction of Serum Uric acid levels at the end of 8 weeks treatment were compared among the 4 treatment groups, it the patients in the *Terminalia bellerica* group reported any adverse effects. However, no subjects discontinued the study due to adverse events.

It can be concluded from the present study that treatment for 8 weeks with *Terminalia chebula* 500 mg BID and *Terminalia bellerica* 500 mg BID had significant effect on lowering Serum Uric acid levels compared to baseline as well as placebo. The clinical study is being continued and it is further expected that after 12 weeks of treatment, the *Terminalia bellerica* 500 mg group and *Terminalia chebula* 500 mg group will demonstrate a further improvement in uric acid reduction, as indicated by a significant drop from 4 weeks to 8 weeks. It is further expected that after 12 weeks, the *Terminalia bellerica* 500 mg BID group and *Terminalia chebula* 500 mg BID group will produce improved serum uric acid levels to about ≤6.0 mg/dl. Additionally, both extracts may work reasonably well at lower doses as well.

It has been demonstrated that the extracts of *T. chebula* and *T. Billerica* each independently can provide substantial improvements in uric acid levels as a treatment for hyperuricemia. It has thus been established that extracts of *T. chebula* and *T. Billerica* are effective xanthine oxidase inhibitors.

Suitable dosages of the *T. chebula* and *T. Billerica* extracts as described herein can range from about 250 mg to about 2000 mg for oral administration to human patients on a daily basis. Another suitable dosage range for *T. chebula* and *T. Billerica* extracts as described herein can range from about 500 mg to about 1000 mg for oral administration to human patients on a daily basis.

The compositions of the present invention may be formulated into nutraceutical or pharmaceutical oral solid dosage forms, such as tablets, capsules, powders or into liquid formulations, such as solutions and suspensions using suitable excipients.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A method of treating a free radical-induced disease in an individual in need thereof comprising administering to the individual a therapeutically effective amount of a composition consisting essentially of an aqueous extract of *Terminalia bellirica*,
   wherein the aqueous extract comprises at least 15% of one or more bioactive low molecular weight hydrolyzable tannins selected from the group consisting of chebulinic acid and chebulagic acid based on the total weight of the extract,
   wherein the administered composition inhibits xanthine oxidase activity, and
   wherein the free radical-induced disease is selected from the group consisting of gout, uricemia, and hyperuricemia.

2. The method of claim 1, wherein the aqueous extract composition comprises not less than about 2% by weight of chebulinic acid based on the total weight of the extract, not less than about 2% by weight of chebulagic acid based on the total weight of the extract, and not less than about 10% by weight other low molecular weight hydrolyzable tannoids based on the total weight of the extract.

3. The method of claim 2, wherein the composition has an effective dose ($ED_{50}$) of about 5 µg/ml for inhibition of xanthine oxidase.

4. A method of treating hyperuricemia in a human individual in need thereof comprising orally administering to the human individual a therapeutically effective amount of a composition consisting essentially of an aqueous extract of *Terminalia bellirica*,
   wherein the aqueous extract comprises at least 15% of one or more bioactive low molecular weight hydrolyzable tannins selected from the group consisting of chebulinic acid and chebulagic acid based on the total weight of the extract; and
   wherein the serum uric acid level in the individual is lowered.

5. The method of claim 4, wherein serum uric acid is lowered to less than about 6.8 mg/dl.

6. The method of claim 4, wherein serum uric acid is lowered to less than about 6.0 mg/dl.

7. The method of claim 4, wherein the aqueous extract comprises not less than about 2% by weight of chebulinic acid based on the total weight of the extract, not less than about 2% by weight of chebulagic acid based on the total weight of the extract, and not less than about 10% by weight other low molecular weight hydrolyzable tannoids based on the total weight of the extract.

8. The method of claim 7, wherein the composition is provided in a daily dosage range of from about 250 mg to about 2000 mg.

9. The method of claim 7, wherein the composition is provided in a daily dosage range of from about 500 mg to about 1000 mg.

10. The method of claim 9, wherein serum uric acid is lowered to less than about 6.8 mg/dl.

11. The method of claim 9, wherein serum uric acid is lowered to less than about 6.0 mg/dl.

* * * * *